US00PP08522P

United States Patent [19]

Trees

[11] Patent Number: Plant 8,522

[45] Date of Patent: Dec. 28, 1993

[54] GERANIUM PLANT 'DESIGNER CORAL'

[75] Inventor: Scott C. Trees, Nipomo, Calif.

[73] Assignee: Ball Floraplant, West Chicago, Ill.

[21] Appl. No.: 996,112

[22] Filed: Dec. 23, 1992

[51] Int. Cl.[5] ..... A01H 5/00
[52] U.S. Cl. ..... Plt./87.12
[58] Field of Search ..... Plt./87.12

[56] References Cited

U.S. PATENT DOCUMENTS

P.P. 7,934 8/1992 Hanes ..... Plt. 87.12

*Primary Examiner*—James R. Feyrer
*Attorney, Agent, or Firm*—Arnold, White & Durkee

[57] ABSTRACT

Geranium Designer Series TM Coral (BFP-360) is a new and distinct cultivar of geranium, botanically known as *Pelargonium* × *hortorum* Bailey. BFP-360 was selected from among the progeny of a cross between female parent 538-1 and male parent Plaisire. The new cultivar is distinguishable from other geraniums and both parents in color and in not requiring a growth regulator to obtain basal branching, compact plants.

1 Drawing Sheet

BACKGROUND OF THE NEW PLANT

Designer Coral is a product of a planned breeding program which had the objective of creating new geranium cultivars with medium green zoned foliage, large round umbels, compact basal branching habit that requires no growth regulators, is fast rooting, and withstands shipping.

Designer Coral was originated from a hybridization made in a controlled breeding program in West Chicago, Ill. The female parent was seedling 538-1, having a semi-double coral-orange flower and dark green foliage. The male parent of BFP-360 was Plaisire (U.S. Plant Pat. No. 6,708), a plant with a semi-double medium salmon flower and green zoned foliage.

Female parent 538-1 is a proprietary line selected from a segregating population. Male parent Plaisire is a European bred variety.

By comparison with Americana Coral which has 5–6 petals, Designer Coral has 5–7 petals. Designer Coral has clean straight peduncles, whereas American Coral often displays a large vestigial node at the base of the peduncle. Americana Coral has a denser canopy than Designer Coral.

Designer Coral further differs from Americana Coral in the following characteristics:

(1) Designer Coral has a more spreading habit in the field compared to a more upright mounded habit for Americana Coral.

(2) Average umbel diameter for Designer Coral is 10.5–11.0 cm compared with 9.5–10.0 cm for Americana Coral.

(3) Designer Coral has a longer peduncle (18.0–18.5 cm) compared with a shorter peduncle for Americana Coral (14.0–14.5 cm ).

(4) Designer Coral has fewer umbels per plant in the field (13) than Americana Coral (16) but has a larger number of florets per umbel (31) compared with Americana Coral (28).

(5) Designer Coral exhibits distinct leaf zonation where the outer half of each leaf is distinctly darker (139A) compared to its basal half (137B) while Americana Coral is overall the same color (137A).

Designer Coral was discovered and selected as one flowering plant within the progeny of the stated cross by the inventor in a controlled environment in Santa Maria, Calif.

The first act of asexal reproduction of Designer Coral was accomplished when vegetative cuttings were taken from the initial selection in a controlled environment in Santa Maria, Calif. by a technician supervised by the inventor. Horticultural examination of selected units demonstrated that the combination of characteristics as herein disclosed for Designer Coral are firmly fixed and are retained through successive generations of asexual reproduction.

Designer Coral has not been observed under all possible environmental conditions. The phenotype may vary significantly with variations in environment such as temperature, light intensity, and day length. The following observations, measurements and comparisons describe plants grown in Arroyo Grande, Calif. under greenhouse conditions which approximate those generally used in commerical practice.

The following traits have been repeatedly observed and are determined to be basic characteristics of Designer Coral which in combination distinguish this geranium as a new and distinct cultivar. These traits include no growth regulators required to obtain basal branching compact plants, a plant height of about 25 cm, a plant width of about 45 cm, clean and straight peduncles without vestigial nodes.

Of the many commercial cultivars known to the present inventor, the most similar in comparison to Designer Coral is Americana Coral (U.S. Plant Pat. No. 7,934). Designer Coral has a coral color similar to that of Americana Coral but has a larger diameter umbel, a longer peduncle, fewer umbels per plant in the field. Designer Coral has a larger number of florets per umbel and is somewhat shorter and wider as a field grown plant. Designer Coral is quite distinguished in appearance from Americana Coral which has a distinct "eye" of lighter coral shade at the base of each petal whereas Designer Coral appears to have an "eye" because the color of the petal attachments and anther filaments are a much lighter color than that of the rest of the petal (color 41A) while the "eye" color is a very light coral (49C). Additionally, Designer Coral has clean straight peduncles compared to Americana Coral which often displays a vestigial node on the base of the peduncle.

DESCRIPTION OF THE PHOTOGRAPH

The accompany color photographs show a top view of the typical flower and foliage characteristics of Designer Coral. The view taken against a dark background illustrates flower color closest to the color values assigned from the Royal Horticultural Society Colour Chart. The view taken against a light background highlights the leaf characteristics.

DESCRIPTION OF THE PLANT

In the following description, color references are made to the Royal Horticulatural Society Colour Chart. The color values were determined 9:00 a.m. on Nov. 10, 1992 under 600 foot candles at Arroyo Grande, Calif. USA.

Classification:

*Botanical.*—*Pelargonium*×*hortorum* Bailey.

*Commercial.*—Designer Coral.

INFLORESCENCE

Umbel:

*Average diameter.*—10.5–11.0 cm.

*Average depth.*—7.5–8.0 cm.

*Peduncle length.*—18.0–18.5 cm with no vestigial node.

*Pedicel length.*—3.2–3.5 cm.

*Number umbels/plant (designate circumstances).*—11–13 on 18 week old field grown plant.

*Number of flowers/umbel.*—31.

Corolla:

*Number of petals.*—5–7.

*Petal size.*—2.5–2.8 cm×2.1–2.2 cm.

*Average diameter.*—4.5–4.7 cm.

*Form.*—Semi-double with petaloids.

*Number of petaloids.*—1–3.

*Size of petaloids.*—Length: 1.0–1.8 cm. width: 0.1–1.6 cm.

*Color (General tonality from a distance of three meters).*—41A — Coral.

*Description of petal form.*—Imbricate.

*Color (abaxial).*—41A.

*Color (adaxial).*—41C.

Bud:

*Shape.*—Oval-pointed.

*Color (abaxial).*—43B.

*Color (adaxial).*—43C.

Reproductive organs:

*Androecium.*—8 Semi-fused 8–9 mm anther/filaments, 2.0–2.5 mm anther (Pollen — 50A).

*Gynoecium.*—11 mm, 5 lobed stigma, 5 mm style.

*Presence or absence of fruits.*—No fruit set.

Spring flowering response period: 7–8 weeks from rooted cuttings.

Outdoor flower production: Extremely freely flowering continuous.

Durability: Some tolerance to Botrytis and weather.

Foliage:

*Leaves (mature).*—11.0–13.0 cm at widest point; 6.0–6.5 cm at narrowest point.

*Leaf stems (pedicles).*—4.6–5.2 cm.

*Pedicles.*—Straight, clean.

*Form.*—Reniform, cordate.

*Margin.*—Crenate.

*Color (abaxial).*—139A leaf margin; 137B leaf base.

*Color (adaxial).*—137C.

*Color* (zonation).—Slight.

*Tolerance of botrytis.*—Good.

General appearnace and form:

*Internode length.*—5.08 cm.

*Branching pattern.*—Spreading habit.

*Height.*—25 cm on 18 week old field grown plants.

What is claimed is:

1. A new and distinct geranium cultivar, substantially as herein described and shown, characterized by its solid coral color, clean straight peduncles and basal branching in the absence of growth regulators.

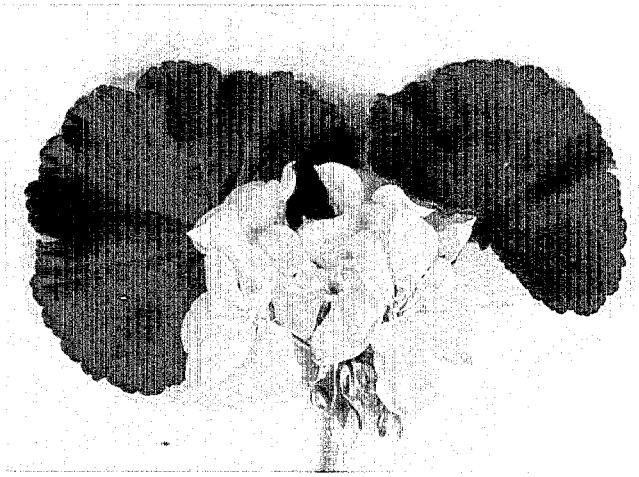
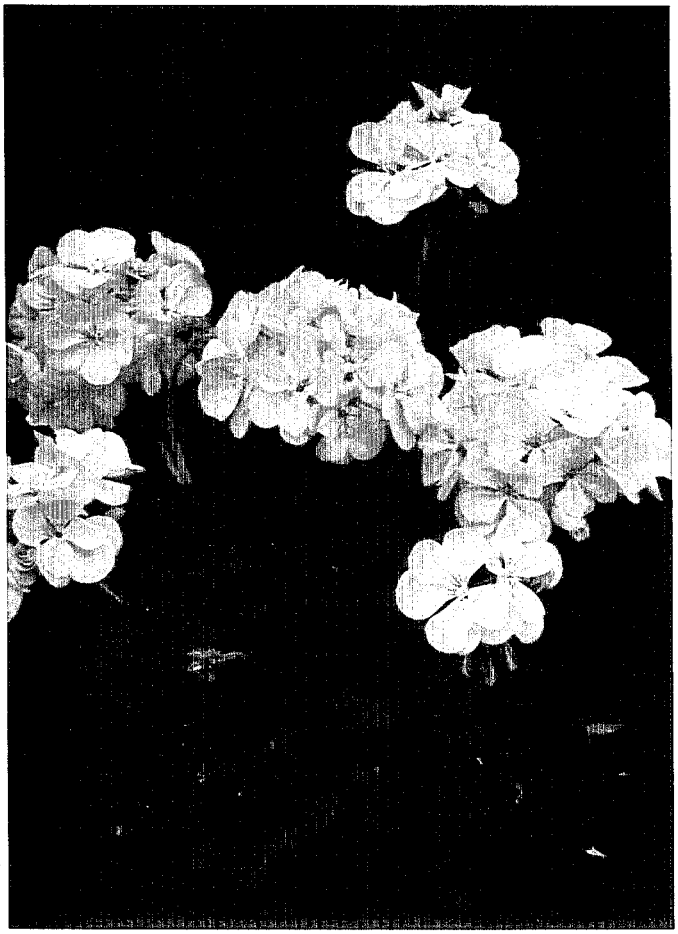

* * * * *